United States Patent
Miller et al.

(10) Patent No.: US 7,273,826 B2
(45) Date of Patent: *Sep. 25, 2007

(54) EPOXIDATION CATALYST

(75) Inventors: Jay F. Miller, Chester Springs, PA (US); Bernard Cooker, Malvern, PA (US); Robert N. Cochran, West Chester, PA (US); Peter J. Whitman, Glen Mills, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 34 days.

This patent is subject to a terminal disclaimer.

(21) Appl. No.: 11/190,088

(22) Filed: Jul. 26, 2005

(65) Prior Publication Data

US 2007/0027347 A1 Feb. 1, 2007

(51) Int. Cl.
*B01J 29/06* (2006.01)
*B01J 29/78* (2006.01)

(52) U.S. Cl. .............. 502/60; 502/63; 502/64; 502/69

(58) Field of Classification Search .......... 502/60, 502/63, 64, 69
See application file for complete search history.

(56) References Cited

U.S. PATENT DOCUMENTS

| 3,351,635 A | 11/1967 | Kollar | 260/348.5 |
|---|---|---|---|
| 4,367,342 A | 1/1983 | Wulff et al. | 549/529 |
| 4,410,501 A | 10/1983 | Taramasso et al. | 423/326 |
| 4,824,976 A | 4/1989 | Clerici et al. | 549/531 |
| 4,833,260 A | 5/1989 | Neri et al. | 549/531 |
| 5,214,168 A * | 5/1993 | Zajacek et al. | 549/531 |
| 5,859,265 A | 1/1999 | Müller et al. | 549/531 |
| 6,005,123 A | 12/1999 | Dessau et al. | 549/531 |
| 6,008,388 A * | 12/1999 | Dessau et al. | 549/531 |
| 6,103,915 A | 8/2000 | Arca et al. | 549/531 |
| 6,399,794 B1 | 6/2002 | Hancu | 549/533 |
| 6,551,546 B1 | 4/2003 | Grosch et al. | 264/621 |
| 6,603,028 B1 * | 8/2003 | Weisbeck et al. | 549/536 |
| 7,182,932 B2 | 2/2007 | Onimus et al. | 423/716 |
| 2003/0073856 A1 * | 4/2003 | Hancu et al. | 549/533 |
| 2004/0068128 A1 * | 4/2004 | Teles et al. | 549/531 |
| 2005/0014635 A1 * | 1/2005 | Zhou et al. | 502/159 |

FOREIGN PATENT DOCUMENTS

| BE | 1001038 A7 | 6/1989 |
|---|---|---|
| GB | 2331071 | 5/1999 |
| JP | 4-352771 | 12/1992 |
| WO | WO 98/00413 | 1/1998 |

* cited by examiner

*Primary Examiner*—Elizabeth D. Wood
(74) *Attorney, Agent, or Firm*—Kevin M. Carroll

(57) ABSTRACT

The invention is a catalyst comprising a titanium or vanadium zeolite, a binder, and zinc oxide, wherein the catalyst is preparing an aqueous mixture of the zeolite, a binder source, and a zinc oxide source, and subjecting the mixture to rapid drying. The catalyst is useful in olefin epoxidation.

7 Claims, No Drawings

EPOXIDATION CATALYST

FIELD OF THE INVENTION

This invention relates to a catalyst which comprises a titanium or vanadium zeolite, a binder, and zinc oxide, that is produced by preparing an aqueous mixture of the titanium or vanadium zeolite, a binder source, and a zinc oxide source, and subjecting the mixture to rapid drying. The catalyst is useful in olefin epoxidation. Surprisingly, the addition of zinc oxide results in decreased ring-opening of the epoxide product and thus lowers selectivity to by-product glycols and glycol ethers.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide oxidizing agent, such as ethylbenzene hydroperoxide or tert-butyl hydroperoxide, is commercially practiced technology. This process is performed in the presence of a solubilized molybdenum catalyst, see, e.g., U.S. Pat. No. 3,351,635, or a heterogeneous titania on silica catalyst, see, e.g., U.S. Pat. No. 4,367,342. Another commercially practiced technology is the direct epoxidation of ethylene to ethylene oxide by reaction with oxygen over a silver catalyst. Unfortunately, the silver catalyst has not proved useful in commercial epoxidation of higher olefins.

Besides oxygen and alkyl hydroperoxides, another oxidizing agent useful for the preparation of epoxides is hydrogen peroxide. U.S. Pat. No. 4,833,260, for example, discloses the epoxidation of olefins with hydrogen peroxide in the presence of a titanium silicate catalyst.

Much current research is conducted in the direct epoxidation of olefins with oxygen and hydrogen. In this process, it is believed that oxygen and hydrogen react in situ to form an oxidizing agent. Many different catalysts have been proposed for use in the direct epoxidation of higher olefins. Typically, the catalyst comprises one or more noble metals supported on a titanosilicate. For example, JP 4-352771 discloses the formation of propylene oxide from propylene, oxygen, and hydrogen using a catalyst containing a Group VIII metal such as palladium on a crystalline titanosilicate. The Group VIII metal is believed to promote the reaction of oxygen and hydrogen to form an in situ oxidizing agent. U.S. Pat. No. 5,859,265 discloses a catalyst in which a platinum metal, selected from Ru, Rh, Pd, Os, Ir and Pt, is supported on a titanium or vanadium silicalite. Other direct epoxidation catalyst examples include gold supported on titanosilicates, see for example PCT Intl. Appl. WO 98/00413.

One disadvantage of the described direct epoxidation catalysts is that they are prone to produce by-products such as glycols or glycol ethers formed by the ring-opening of the epoxide product or alkane by-product formed by the hydrogenation of olefin. U.S. Pat. No. 6,008,388 describes a direct olefin epoxidation process in which the selectivity for the reaction of olefin, oxygen, and hydrogen in the presence of a noble metal-modified titanium zeolite is enhanced by the addition of a nitrogen compound such as ammonium hydroxide to the reaction mixture. U.S. Pat. No. 6,399,794 teaches the use of ammonium bicarbonate modifiers to decrease the production of ring-opened by-products. U.S. Pat. No. 6,005,123 teaches the use of phosphorus, sulfur, selenium or arsenic modifiers such as benzothiophene to decrease the production of propane.

As with any chemical process, it is desirable to attain still further improvements in the epoxidation methods and catalysts. We have discovered a new epoxidation catalyst and its use in the epoxidation of olefins.

SUMMARY OF THE INVENTION

The invention is a catalyst comprising a titanium or vanadium zeolite, a binder, and zinc oxide, wherein the catalyst is produced by preparing an aqueous mixture of the zeolite, a binder source, and a zinc oxide source, and subjecting the mixture to rapid drying. The invention also includes the use of the catalyst in olefin epoxidation.

DETAILED DESCRIPTION OF THE INVENTION

The catalyst of the invention comprises a titanium or vanadium zeolite, a binder, and zinc oxide, and is produced by a rapid drying procedure. Rapid drying titanium or vanadium zeolites to form microspheres of particle size greater than about 5 um is well known, see for example, U.S. Pat. Nos. 4,824,976 and 6,551,546.

The catalyst of the invention is formed by preparing an aqueous mixture of the titanium or vanadium zeolite, a binder source, and a zinc oxide source, and subjecting the mixture to rapid drying.

Titanium or vanadium zeolites comprise the class of zeolitic substances wherein titanium or vanadium atoms are substituted for a portion of the silicon atoms in the lattice framework of a molecular sieve. Such substances, and their production, are well known in the art. See for example, U.S. Pat. Nos. 4,410,501 and 4,833,260. Particularly preferred titanium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium-containing molecular sieves having framework structures isomorphous to zeolite beta, mordenite, ZSM-48, ZSM-12, MCM-22(MWW), and MCM-41 are also suitable for use. The titanium zeolites preferably contain no elements other than titanium, silicon, and oxygen in the lattice framework, although minor amounts of boron, iron, aluminum, sodium, potassium, copper and the like may be present.

The binder is any suitable binder useful for agglomerating titanium or vanadium zeolite particles, and imparting improved mechanical properties to the zeolite. Preferred binders include the oxides of silicon, aluminum, boron, phosphorus, titanium, zirconium and/or magnesium. Especially preferred binders are silica, alumina, titania, calcium phosphate, calcium silicate, clay minerals, and mixtures thereof. Examples of clay minerals include montmorillonites, kaolins, bentonites and sepiolites. Preferred binder sources include silica sources, alumina sources, and the like. Silica sources include, but are not limited to, colloidal silica, fumed silica, silicon alkoxides, alkali and alkaline earth metal silicates. Preferred silicon alkoxides include tetraethylorthosilicate, tetramethylorthosilicate, and the like. Tetraethylorthosilicate is especially preferred. Silica sources also include oligomeric silica formed by the hydrolysis of a silicon alkoxides, such as tetraethylorthosilicate, in the presence of a tetraalkylammonium hydroxide. Preferred alkali and alkaline earth metal silicates include calcium silicate, sodium silicate, potassium silicate, and magnesium silicate. Suitable alumina sources include aluminum trialkoxides such as aluminum triisopropoxide. Suitable binder sources also include titania sources (such as titanates and titania sol), clay mineral sources (such as kaolin), and calcium phosphate.

Zinc oxide sources are zinc-containing compounds that form zinc oxide when subjected to a rapid drying procedure and, preferably, a high temperature calcination. Preferred zinc oxide sources include zinc oxide, as well as zinc compounds such as zinc nitrate, zinc acetate, zinc formate, zinc nitrite, zinc oxalate, zinc butyrate, zinc carbonate, zinc citrate, zinc hydroxide, zinc lactate, zinc laurate and zinc oleate.

The aqueous mixture is prepared by dispersing the titanium or vanadium zeolite, the binder source, and the zinc oxide source in water. The aqueous mixture preferably contains from 1-10 wt. % binder source, 0.01-5 wt. % zinc oxide source, and 10-30 wt. % titanium or vanadium zeolite. The order of addition is not considered to be critical, but preferably, the aqueous mixture is prepared by dispersing the titanium or vanadium zeolite in water and mixing to eliminate lumps, then combining with the binder source, followed by the zinc oxide source. The total solids content in the aqueous mixture is preferably 10-30 wt. %. If necessary, the solids in the dispersion may be ground to a particle size which is appropriate for feeding a spray dryer, for example 1-2 microns. Preferably, the aqueous mixture is passed through an appropriate screen, e.g. 100 mesh, to ensure that unduly large particles do not pass to the spray dryer.

After the aqueous mixture is formed, the mixture is then subjected to rapid drying to form the catalyst comprising titanium or vanadium zeolite, binder, and zinc oxide. When the zinc oxide source is a zinc compound (as described above, such as zinc nitrate), the rapid drying procedure includes a calcination step (heating at greater than 250° C.) to convert the zinc compound to zinc oxide. Rapid drying may be accomplished by any known method, including prilling, drying in air on trays (followed by fragmentation and sieving), spray drying, belt roaster drying and calcination (followed by grinding), extrusion, vacuum drying on a belt (followed by calcination and grinding). Preferably, the rapid drying is performed by means of a spray dryer. By submitting the aqueous mixture to rapid drying, water is eliminated and simultaneously the binder is activated, leading to the formation of microspheres with a three-dimensional lattice, wherein the crystallites of zeolite are closely encaged by, e.g., Si—O—Si, Al—O—Al, or Si—O—Al bridges. Typically, a 5-100 micron dry product is produced.

The catalyst of the invention preferably comprises 50-90 weight percent titanium or vanadium zeolite, 10-50 weight percent silica or alumina binder, and 0.1-2 weight percent zinc oxide Before being employed in epoxidation, the catalyst is preferably calcined or pyrolyzed, preferably in an oxygen containing atmosphere, at 300-800° C., more preferably from 300-650° C.

One epoxidation process of the invention comprises contacting an olefin and hydrogen peroxide in the presence of the catalyst of the invention. Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing $C_2$-$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

The hydrogen peroxide may be generated prior to use in the epoxidation reaction. Hydrogen peroxide may be derived from any suitable source, including oxidation of secondary alcohols such as isopropanol, the anthraquinone process, and from direct reaction of hydrogen and oxygen. The concentration of the aqueous hydrogen peroxide reactant added into the epoxidation reaction is not critical. Typical hydrogen peroxide concentrations range from 0.1 to 90 weight percent hydrogen peroxide in water, preferably 1 to 5 weight percent.

The amount of hydrogen peroxide to the amount of olefin is not critical, but most suitably the molar ratio of hydrogen peroxide:olefin is from 100:1 to 1:100, and more preferably in the range of 10:1 to 1:10. One equivalent of hydrogen peroxide is theoretically required to oxidize one equivalent of a mono-unsaturated olefin substrate, but it may be desirable to employ an excess of one reactant to optimize selectivity to the epoxide.

The hydrogen peroxide may also be generated in situ by the reaction of hydrogen and oxygen in the presence of a noble metal catalyst. Although any sources of oxygen and hydrogen are suitable, molecular oxygen and molecular hydrogen are preferred.

While any noble metal catalyst can be utilized (i.e., gold, silver, platinum, palladium, iridium, ruthenium, osmium metal catalysts), either alone or in combination, palladium, platinum and gold metal catalysts are particularly desirable. Suitable noble metal catalysts include high surface area noble metals, noble metal alloys, and supported noble metal catalysts. Examples of suitable noble metal catalysts include high surface area palladium and palladium alloys. However, particularly preferred noble metal catalysts are supported noble metal catalysts comprising a noble metal and a support.

For supported noble metal catalysts, the support is preferably a porous material. Supports are well-known in the art. There are no particular restrictions on the type of support that are used. For instance, the support can be inorganic oxides, inorganic chlorides, carbon, and organic polymer resins. Preferred inorganic oxides include oxides of Group 2, 3, 4, 5, 6, 13, or 14 elements. Particularly preferred inorganic oxide supports include silica, alumina, titania, zirconia, niobium oxides, tantalum oxides, molybdenum oxides, tungsten oxides, amorphous titania-silica, amorphous zirconia-silica, amorphous niobia-silica, and the like. Preferred organic polymer resins include polystyrene, styrene-divinylbenzene copolymers, crosslinked polyethyleneimines, and polybenzimidizole. Suitable supports also include organic polymer resins grafted onto inorganic oxide supports, such as polyethylenimine-silica. Preferred supports also include carbon. Particularly preferred supports include carbon, silica, silica-aluminas, titania, zirconia, and niobia.

Preferably, the support has a surface area in the range of about 10 to about 700 $m^2/g$, more preferably from about 50 to about 500 $m^2/g$, and most preferably from about 100 to about 400 $m^2/g$. Preferably, the pore volume of the support is in the range of about 0.1 to about 4.0 mL/g, more preferably from about 0.5 to about 3.5 mL/g, and most preferably from about 0.8 to about 3.0 mL/g. Preferably, the average particle size of the support is in the range of about 0.1 to about 500 μm, more preferably from about 1 to about 200 pm, and most preferably from about 10 to about 100 μm. The average pore diameter is typically in the range of about 10 to about 1000 Å, preferably about 20 to about 500 Å, and most preferably about 50 to about 350 Å.

The supported noble metal catalyst contains a noble metal. While any of the noble metals can be utilized (i.e., gold, silver, platinum, palladium, iridium, ruthenium, osmium), either alone or in combination, palladium, platinum and gold are particularly desirable. Typically, the amount of noble metal present in the supported catalyst will be in the range of from 0.001 to 20 weight percent, preferably 0.005 to 10 weight percent, and particularly 0.01 to 5 weight percent. The manner in which the noble metal is incorporated into the supported catalyst is not considered to be particularly critical. For example, the noble metal may be supported by impregnation, adsorption, precipitation, or the like. Alternatively, the noble metal can be incorporated by ion-exchange with, for example, tetraamine palladium dinitrate.

There are no particular restrictions regarding the choice of noble metal compound or complex used as the source of the noble metal in the supported catalyst. For example, suitable compounds include the nitrates, sulfates, halides (e.g., chlorides, bromides), carboxylates (e.g. acetate), and amine complexes of noble metals.

In one preferred embodiment of the invention, the epoxidation of olefin, hydrogen and oxygen is carried out in the presence of a noble metal-containing titanium or vanadium zeolite which comprises a noble metal and the catalyst of the invention. In this embodiment, the catalyst of the invention functions as a support for the noble metal. The manner in which the noble metal is incorporated into the catalyst of the invention is not considered to be particularly critical. For example, the noble metal may be supported by impregnation, adsorption, precipitation, or the like. Alternatively, the noble metal can be incorporated by ion-exchange with, for example, tetraamine palladium dinitrate. While any of the noble metals can be utilized (i.e., gold, silver, platinum, palladium, iridium, ruthenium, osmium), either alone or in combination, palladium, platinum and gold are particularly desirable. Typically, the amount of noble metal present in the noble metal-containing zeolite will be in the range of from 0.001 to 20 weight percent, preferably 0.005 to 10 weight percent, and particularly 0.01 to 5 weight percent.

Depending on the olefin to be reacted, the epoxidation according to the invention can be carried out in the liquid phase, the gas phase, or in the supercritical phase. When a liquid reaction medium is used, the catalyst is preferably in the form of a suspension or fixed-bed. The process may be performed using a continuous flow, semi-batch or batch mode of operation.

If epoxidation is carried out in the liquid (or supercritical) phase, it is advantageous to work at a pressure of 1-100 bars and in the presence of one or more solvents. Suitable solvents include, but are not limited to, alcohols, ketones, water, $CO_2$, or mixtures thereof. Suitable alcohols include $C_1$-$C_4$ alcohols such as methanol, ethanol, isopropanol, and tert-butanol, or mixtures thereof. If $CO_2$ is used as a solvent, the $CO_2$ may be in the supercritical state or in a high pressure/subcritical state. Fluorinated alcohols can be used. It is preferable to use mixtures of the cited alcohols with water.

If epoxidation is carried out in the liquid (or supercritical) phase, it is advantageous to use a buffer. The buffer will typically be added to the solvent to form a buffer solution. The buffer solution is employed in the reaction to inhibit the formation of glycols or glycol ethers during epoxidation. Buffers are well known in the art.

Buffers useful in this invention include any suitable salts of oxyacids, the nature and proportions of which in the mixture, are such that the pH of their solutions may preferably range from 3 to 12, more preferably from 4 to 10 and most preferably from 5 to 9. Suitable salts of oxyacids contain an anion and cation. The anion portion of the salt may include anions such as phosphate, carbonate, bicarbonate, carboxylates (e.g., acetate, phthalate, and the like), citrate, borate, hydroxide, silicate, aluminosilicate, or the like. The cation portion of the salt may include cations such as ammonium, alkylammoniums (e.g., tetraalkylammoniums, pyridiniums, and the like), alkali metals, alkaline earth metals, or the like. Cation examples include $NH_4$, $NBu_4$, $NMe_4$, Li, Na, K, Cs, Mg, and Ca cations. Buffers may preferably contain a combination of more than one suitable salt. Typically, the concentration of buffer in the solvent is from about 0.0001 M to about 1 M, preferably from about 0.0005 M to about 0.3 M. The buffer useful in this invention may also include the addition of ammonia gas or ammonium hydroxide to the reaction system. For instance, one may use a pH=12-14 solution of ammonium hydroxide to balance the pH of the reaction system. More preferred buffers include alkali metal phosphate, ammonium phosphate, and ammonium hydroxide buffers.

The process of the invention may be carried out in a batch, continuous, or semi-continuous manner using any appropriate type of reaction vessel or apparatus such as a fixed-bed, transport bed, fluidized bed, stirred slurry, or CSTR reactor. The catalyst is preferably in the form of a suspension or fixed-bed. Known methods for conducting metal-catalyzed epoxidations of olefins using an oxidizing agent will generally also be suitable for use in this process. Thus, the reactants may be combined all at once or sequentially.

Epoxidation according to the invention is carried out at a temperature effective to achieve the desired olefin epoxidation, preferably at temperatures in the range of 0-150° C., more preferably, 20-120° C. Reaction or residence times of from about 1 minute to 48 hours, more preferably 1 minute to 8 hours will typically be appropriate. It is advantageous to work at a pressure of 1 to 100 atmospheres, although the reaction can also be performed at atmospheric pressure.

The following examples merely illustrate the invention. Those skilled in the art will recognize many variations that are within the spirit of the invention and scope of the claims.

EXAMPLE 1

Preparation of Pd/TS-1 Catalysts

Catalyst 1A: A mixture of 79.1 wt. % TS-1 (previously calcined at 550° C.), 20 wt. % colloidal silica binder, and 1.1 wt. % zinc oxide (Kadox 911) is added to water to form a 21 wt. % slurry of a catalyst mixture. The slurry is continuously fed from an agitated feed tank at ambient temperature, via a variable speed screw pump, to the rotary atomizer wheel of spray dryer. The rotary atomizer is run at 15,000 RPM, with a slurry feed rate of 0.208 to 0.217 gpm, and an air feed temperature is 416 to 437° C. (780 to 819F). The feed is atomized in the top of the upper, cylindrical, section of the spray dryer and descends through the lower, conical, section to the solids discharge point at the apex of the cone. The resulting spray dried material is dried for 2 hours at 110° C. in air, followed by calcination in air for 4 hours at 550° C. The calcined product contains 0.35 wt. % zinc and 1.42 wt. % Ti.

Palladium is applied to the spray dried TS-1 by ion exchange. Tetraaminepalladium dichloride hydrate (0.80 g)

is added to water (54 g), and this solution is then added the spray dried catalyst (200 g, slurried in 393 g of water). After two hours of gentle agitation at 30° C., the catalyst is filtered, washed, and then dried. The resulting catalyst is calcined in air at 300° C. for 4 hours, then reduced under hydrogen for 4 hours at 50° C. to give Catalyst 1A. Catalyst 1A contains 0.26 wt. % Zn, 1.4 wt. % Ti, and 0.15 wt. % Pd.

Comparative Catalyst 1B: Catalyst 1B is prepared by spray drying an 80 wt. % mixture of TS-1 and 20 wt. % silica binder (no zinc oxide or compounds are used) and applying palladium to the spray dried particles according to the procedure of Catalyst 1A. Comparative Catalyst 1B contains 1.9 wt. % Ti and 0.10 wt. % Pd.

Catalyst 1C: Catalyst 1C is prepared using the same calcined (spray dried) product as in the Catalyst 1A preparation, and applying palladium to the spray dried particles according to the procedure of Catalyst 1A with the exception that only 0.4 g of tetraaminepalladium dichloride hydrate is used. Catalyst 1C contains and 1.3 wt. % Ti, 0.26% Zn, and 0.09 wt. % Pd.

Comparative Catalyst 1D: Catalyst 1D is prepared by spray drying a 40 wt. % aqueous slurry (80 wt. % TS-1 and 20 wt. % colloidal silica binder) according to the procedure of Catalyst 1A, except that the slurry feed rate is 0.167 gpm, and the air feed temperature is 376° C. (708F).

Palladium is applied to the spray dried TS-1 by ion exchange. Tetraaminepalladium dichloride hydrate (0.37 g) is added to water (400 g), and this solution is then added the spray dried catalyst (200 g). After heating the mixture at 30° C. under agitation for 16 hours, the catalyst is filtered, washed (2×500 g water), and then dried. The resulting catalyst is dried overnight in a vacuum oven at 50° C., heated at 110° C. for 2 hours, calcined in air at 300° C. for 4 hours, then reduced under hydrogen (4 vol. % hydrogen in nitrogen) for 4 hours at 50° C. to give Catalyst 1D. Comparative Catalyst 1D contains 2.1 wt. % Ti, and 0.063 wt. % Pd.

Comparative Catalyst 1E: Zinc nitrate is added by incipient wetness to spray dried TS-1 by the following impregnation procedure. Zinc nitrate hexahydrate (6.427 g) in deionized water (200 g) is added to the calcined spray dried TS-1 produced in Comparative Catalyst 1D (200 g), then the mixture is heated in air at 110° C. for 2 hours and calcined in air at 550° C. for 4 hours.

Palladium is applied to the zinc-impregnated TS-1 by ion exchange by the procedure described in Comparative Catalyst 1D. Comparative Catalyst 1E contains 0.25 wt. % Zn, 2.0 wt. % Ti, and 0.065 wt. % Pd.

EXAMPLE 2

Epoxidation of Propylene

Catalysts 1A-1C Runs: To evaluate Catalysts 1A-1C, the epoxidation of propylene using oxygen and hydrogen is carried out. The following procedure is employed.

The reaction system consists of a 1000-cc stainless steel CSTR type reactor. Gas and liquid feeds enter the reactor, and the vapor exits the reactor through a port at the top of the reactor, while the liquid exits through a filter which keeps the catalyst in the reactor. Catalyst (60 g) and the reaction solvent (450 mL methanol and 150 mL water) are added to the reactor. This slurry is heated in the reactor to 60° C. under about 500 psig, and is stirred at 500 rpm. Additional reaction solvent is pumped through the reactor at a rate of about 98 g/hr (75 g/hr methanol; 23 g/hr water). Ammonium phosphate solution (pH=7.2, 0.1 M) is added to the reactor through a separate feed line at a rate of about 2 mL/hr resulting in a final buffer concentration 2 mM. The gas flow rates are about 338 SLPH (standard liters per hour) of nitrogen, 300 SLPH of 8 vol. % oxygen in nitrogen containing 1 vol. % methane, 16 SLPH hydrogen, and 75 g/hr propylene.

The gas product exits from the top of the reactor, while the liquid product exits through a filter which contains the catalyst in the reactor. Periodically, samples of the liquid and gaseous effluent are analyzed. Propylene oxide and equivalents ("POE") are produced during the reaction. POE produced include propylene oxide ("PO") and the ring-opened products ("RO") propylene glycol and glycol ethers. The products coming out of the reactor (in both vapor and liquid phase) are analyzed by GC. The results of the GC analyses are used to calculate the PO ring opening rate constant values shown in Table 1.

Catalysts 1D-1E Runs: The reaction system consists of a 1000-cc stainless steel CSTR type reactor. Gas and liquid feeds enter the reactor, and the vapor exits the reactor through a port at the top of the reactor and through a catalyst slurry-immersed filter, which keeps the catalyst in the reactor. The liquid exits through the filter. Catalyst (40 g) and the reaction solvent (400 mL, 85 wt. % methanol and 15 wt. % water) are added to the reactor. This slurry is heated in the reactor at 65° C. under 850 psig, and it is stirred at 500 rpm. Additional reaction solvent (85 wt. % methanol and 15 wt. % water) is pumped through the reactor at a rate of 145 mL/hr (for the Catalyst 1D run) and 170 cc/hr (for the Catalyst 1E run). Dilute aqueous ammonia (0.119 wt. % aqueous ammonia for the Catalyst 1D run; and 0.116 wt. % for the Catalyst 1E run) is added to the reactor through a separate feed line at a rate of 5 mL/hr (Cat. 1D run) and 7.5 mL/hr (Cat. 1E run), resulting in a maximum concentration of ammonia in the reactor exit line of 0.0046 wt. % (Cat. 1D run) and 0.0061 wt. % (Cat. 1E run). The gas flow rates were 4.8 SLPH (standard liters per hour) of nitrogen, 6.8 SLPH of hydrogen, 540 SLPH of 5 vol. % oxygen in nitrogen containing 0.5 vol. % methane and 30 g/hr propylene.

The gas product exits from the top of the reactor and from the top of the gas/liquid separator, which receives the mixture that passes through the reactor filter. Periodically, samples of the liquid and gaseous effluent are analyzed. The products coming out of the reactor (in both vapor and liquid phases) are analyzed by GC. The results of the GC analyses are used to calculate the PO ring opening rate constants which are shown in Table 1

The results of Comparative Catalysts 1D and 1E indicate that a catalyst that incorporates zinc after the spray dried particles are formed results in an even higher ring opening rate compared to a catalyst without zinc. However, the use of a catalyst that incorporates zinc during the spray drying procedure (such as Catalyst 1A or 1C) significantly lowers the ring opening rate compared to catalysts that do not contain zinc such as Comparative Catalyst 1B.

TABLE 1

COMPARISON OF RING OPENING RATES

| Catalyst | Ring Opening Rate Constant [1] | | |
|---|---|---|---|
| | 60° C. | 50° C. | 65° C. |
| 1A | 0.015 | 0.005 | |
| 1B * | 0.037 | 0.01 | |
| 1C | 0.023 | 0.007 | |
| 1D * | | | 0.044 |

TABLE 1-continued

COMPARISON OF RING OPENING RATES

| Catalyst | Ring Opening Rate Constant [1] | | |
|---|---|---|---|
|  | 60° C. | 50° C. | 65° C. |
| 1E * |  |  | 0.165 |

\* Comparative Example
[1] Ring Opening Rate Constant = grams RO produced/gram of catalyst per hour per percent PO in the liquid.

We claim:

1. A catalyst comprising a titanium or vanadium zeolite, palladium, a binder, and zinc oxide, wherein the catalyst is produced by preparing an aqueous mixture of the zeolite, a binder source, and a zinc oxide source, and subjecting the mixture to spray drying.

2. The catalyst of claim 1 wherein the zeolite is a titanium silicalite.

3. The catalyst of claim 1 wherein the zeolite is TS-1.

4. The catalyst of claim 1 wherein the binder is selected from the group consisting of a silica, alumina, titania, calcium phosphate, calcium silicate, clay minerals, and mixtures thereof.

5. The catalyst of claim 1 wherein the binder source is selected from the group consisting of colloidal silica, fumed silica, oligomeric silica, silicon alkoxides, alkali and alkaline earth metal silicates, aluminum trialkoxide, and mixtures thereof.

6. The catalyst of claim 1 wherein the zinc, oxide source is selected from the group consisting of zinc oxide, zinc nitrate, zinc acetate, zinc formate, zinc nitrite, zinc oxalate, zinc butyrate, zinc carbonate, zinc citrate, zinc hydroxide, zinc lactate, zinc laurate, zinc oleate, and mixtures thereof.

7. The catalyst of claim 1 comprising 50-90 weight percent zeolite, 10-50 weight percent binder, and 0.1-2 weight percent zinc oxide.

* * * * *